United States Patent

Engelson et al.

[11] Patent Number: 5,423,849
[45] Date of Patent: Jun. 13, 1995

[54] VASOOCCLUSION DEVICE CONTAINING RADIOPAQUE FIBERS

[75] Inventors: Erik T. Engelson, Menlo Park; Gene Samson, Milpitas, both of Calif.

[73] Assignee: Target Therapeutics, Inc., Fremont, Calif.

[21] Appl. No.: 5,478

[22] Filed: Jan. 15, 1993

[51] Int. Cl.⁶ .............................. A61B 17/00
[52] U.S. Cl. .................. 606/191; 606/198; 604/52
[58] Field of Search ........... 606/191, 195, 198, 200; 623/1, 11; 128/899; 604/52, 53, 57, 60

[56] References Cited

U.S. PATENT DOCUMENTS

| | | |
|---|---|---|
| 3,105,492 | 10/1963 | Jeckel . |
| 3,272,204 | 9/1966 | Artandi et al. . |
| 3,826,171 | 7/1974 | Kaar ................... 84/297 S |
| 4,313,231 | 2/1982 | Koyamada ............... 623/1 |
| 4,364,392 | 12/1982 | Strother et al. . |
| 4,512,338 | 4/1985 | Balko et al. ............. 606/195 |
| 4,629,458 | 12/1986 | Pinchuk ................. 623/1 |
| 4,708,718 | 11/1987 | Daniels ................. 604/53 |
| 4,733,665 | 3/1988 | Palmaz .................. 623/1 |
| 4,798,606 | 1/1989 | Pinchuk ................. 623/1 |
| 4,820,298 | 4/1989 | Leveen et al. ........... 623/1 |
| 4,994,069 | 2/1991 | Ritchart et al. ......... 606/191 |
| 5,071,407 | 12/1991 | Termin et al. ........... 604/104 |
| 5,108,407 | 4/1992 | Geremia et al. .......... 604/57 |
| 5,167,624 | 12/1992 | Butler et al. ........... 606/191 |
| 5,190,546 | 3/1993 | Jervis .................. 606/200 |
| 5,217,484 | 6/1993 | Marks ................... 606/200 |
| 5,226,911 | 7/1993 | Chee et al. ............. 604/52 |
| 5,250,071 | 10/1993 | Palermo ................. 606/198 |
| 5,256,146 | 10/1993 | Ensminger et al. ........ 606/198 |
| 5,261,916 | 11/1993 | Engelson ................ 606/191 |

FOREIGN PATENT DOCUMENTS 2617482  7/1992  France ................... 623/1

*Primary Examiner*—Stephen C. Pellegrino
*Assistant Examiner*—R. Lewis
*Attorney, Agent, or Firm*—Morrison & Foerster

[57] ABSTRACT

This invention is a vasoocclusive device. More particularly, it is a tubular vasoocclusion braid woven from at least radiopaque fibers. The braid may also be partially woven from radiolucent fibers. Optionally, the device may contain a fibrous center or wick in its interior. The device may be continuous or segmented and a fibrous covering or element may be attached.

16 Claims, 2 Drawing Sheets

VASOOCCLUSION DEVICE CONTAINING RADIOPAQUE FIBERS

FIELD OF THE INVENTION

This invention is a vasoocclusive device. More particularly, it is a tubular vasoocclusion braid woven from at least radiopaque fibers. The braid may also be partially woven from radiolucent fibers. Optionally, the device may contain a fibrous center or wick in its interior. The device may be continuous or segmented and a fibrous covering or element may be attached.

BACKGROUND OF THE INVENTION

Vasoocclusion devices are surgical implements that are placed within the vasculature of the human body, typically via a catheter, either to block the flow of blood through the vessel making up that portion of the vasculature or to form a clot within an aneurysm stemming from the vessel. One widely used vasoocclusive device is a helical wire coil having windings that are dimensioned to engage the walls of the vessels. Fibers may also be woven or laid crosswise through the windings to provide a substrate for clot formation and tissue growth within the chosen site. Coils having such a structure are readily commercially available.

U.S. Pat. No. 4,994,069, to Richart et al., describes a vasoocclusive coil which assumes a linear helical configuration when stretched, and a folded convoluted configuration when relaxed. The coil is introduced into the human body in a stretched condition. When the coil reaches its intended site, the coil assumes its relaxed condition—which is better suited to occlude the vessel—and restricts blood flow beyond the space that it occupies.

U.S. Pat. No. 5,226,911, to Chee et al. teaches a helical vasoocclusion coil to which fibrous elements are attached in such a way that they will not be dislodged from the coil. The fibrous elements enhance the ability of the coil to fill space within the vasculature and to facilitate clot formation and tissue growth.

Care must be taken in creating combination fibrous vasoocclusive elements, i.e., those containing multiple cores and fibrous elements, since the fibrous elements may come off and migrate to vessels supplying blood to normal tissue. Fibrous elements, since they are not normally radiopaque, are difficult to find and to retrieve if separated from the metallic coil. Nevertheless, it is desireable to increase the ratio of fibrous element to the metallic coil since the fibrous element increases the tendency of the coil assembly to cause embolic and tissue growth.

The inventive vasoocclusive braid is desireable in that the ratio of fibrous material to metallic material is quite high, the fibrous material is held firmly in place due to the braided or woven configuration, and is easily placed within the body's vasculature.

SUMMARY OF THE INVENTION

This invention is a vasoocclusive device comprising:
(a) a braided member which may be segmented, continuous, or segmented having a gap between the two end portions, but in each case having a first end and a second end and woven at least from radiopaque fibers but optionally partially woven from radiolucent fibers; and optionally (b) at least one fibrous woven element or covering attached to the exterior of the braid, and (c) a fibrous wick or center as the core of the braided member.

DESCRIPTION OF THE INVENTION

Figure 1:
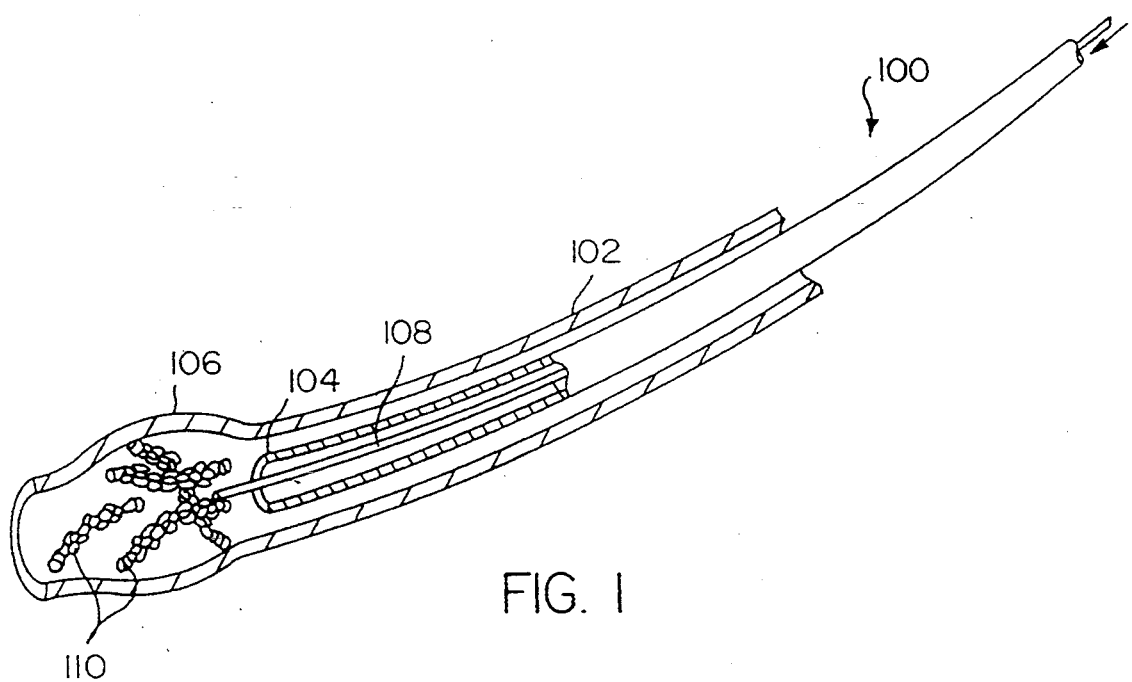
FIG. 1 is a schematic depiction of an overall system for introducing the inventive devices into the vessel of a human body.

The vasoocclusive devices of this invention may be used in a manner similar to those described in U.S. Pat. No. 4,994,069. Briefly, the inventive devices may be supplied in a pre-packaged form in a sterile cannula which is adapted to engage the proximal end of a catheter. As is shown in FIG. 1, once the catheter (100) is in place within a vessel (102)—for instance, the distal end (104) of the catheter (100) at an aneurysm (106)—the braid-containing cannula is placed into engagement with the proximal end of the catheter and the braids are transferred from the cannula lumen into the catheter lumen by exerting force on the proximal end of the coil. A flexible pusher device (108) may be used to push the braid (110) through the catheter (100) to the desired release site. The location of the braids (110) may be observed due to the radiopacity of the metallic strands in the braid. Once at the site, the braids are singly plunged from the catheter lumen into the vessel site (106).

Figure 2:
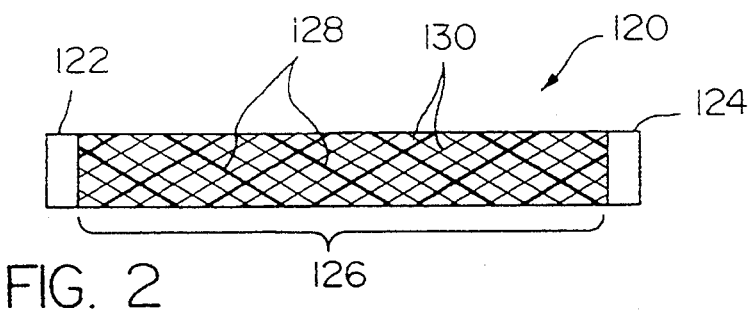
FIGS. 2–5 are side views, partial cross-sectional side views, or partial cutaway sideviews of a number of embodiments of the inventive vasoocclusive device.

FIG. 2 depicts one embodiment of the vasoocclusive braid of the invention, generally shown as (120). The vasoocclusive device (120) has several components: a first end (122), a second end (124), and a braided or woven tubular fibrous element (126) extending from the first end (122) to a similar position on the second end (124). The tubular element (126) may be made up completely or partially of regular or randomly included radiopaque wires (128) and optionally may be partially woven of, or cowoven with, radiolucent fibers or wires (130). The braided member may be woven using known weaving techniques and devices to form the tubular member (126) shown in this and the other figures.

Caps (122) and (124), variously in this configuration and in the others discussed herein, may be made of a radiopaque material such as platinum, tungsten, gold, silver, or alloys thereof, or other suitable generally radiopaque metals which are otherwise biologically inert. Radiopacity for the caps (122) and (124) is, of course, optional since the braid itself contains radiopaque wires. The caps (122) and (124) may be produced from a polymeric material or glue which seals the wires into the fibrous tubular element and keeps it from unraveling.

The diameter of the wire or fiber used in production of the braid will typically be in the range of 0.0005 and 0.005 inches. The resulting woven braid diameter will normally be 0.008 to 0.018 inches. Preferably, the braid diameter is 0.015 to 0.018 inches. The wire may be a radiopaque material such as a metal or polymer, which polymer may be filled with a radiopaque material such as powdered tantalum. Suitable metals and alloys include the platinum group metals especially platinum, rhodium, palladium, and tungsten, gold, silver, tantalum, or alloys thereof. Preferred is a platinum-tungsten alloy.

The wire may also be any of a variety of stainless steels but may be made of other appropriate materials including shape memory or highly elastic alloys such as nickel-titanium alloys (48-58 atomic % nickel and optionally containing modest amounts of iron); copper-zinc alloys (38.5-41.5 weight % zinc); copper-zinc alloys containing 1-10 weight % of beryllium, silicon, tin, aluminum, or gallium; or nickel-aluminum alloys (36-38 atomic % aluminum). Particularly preferred are the alloys described in U.S. Pat Nos. 3,174,851, 3,351,463, and 3,753,700. Especially preferred is the Ti-Ni alloy known as Nitinol. Nitinol wire having the proper transition temperature allows the device to be introduced through the catheter in a linear fashion and upon raising the temperature of the vasoocclusive braid to body temperature, the wire in that braid assumes its preselected shape.

The radiolucent fibers may be made from biocompatible materials such as Dacron (polyester), polyglycolic acid, polylactic acid, fluoropolymers (polytetrafluoroethylene), Nylon (polyamide), or silk. The strands forming the braid should be reasonably heavy, e.g., having tensile strength of greater than about 0.15 pounds. Preferred materials are Dacron strands.

The fibrous elements incorporated into the braid may be a bundle of individual fibers, e.g., between 5 and 100 fibers per fibrous bundle, preferably 20 to 30 fibers per bundle, or may be monofilaments.

The axial length of the braid will usually be in the range of 0.5 to 100 cm, more usually 2.5 to 40 cm.

Figure 3:
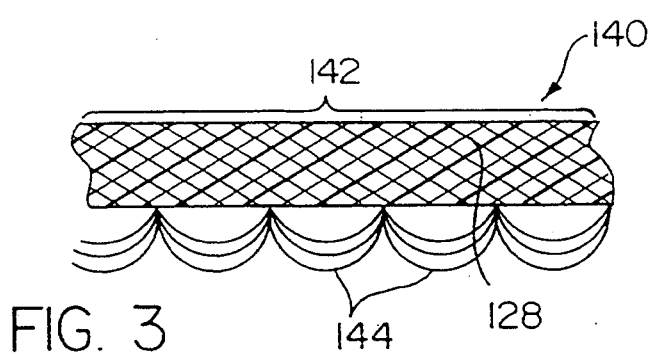

FIG. 3 shows another variation of the inventive vasoocclusive device (140). In this variation, the tubular braid (142) contains a slightly higher incidence of radiopaque wires (128) than the braid shown in FIG. 2. This aspect is shown merely for the purpose of illustration. As noted above, the intent is to include at least radiopaque elements and optionally radiolucent elements which enhance the embolic features of the inventive braid. More importantly, FIG. 3 shows the use of outlying fibers (144) which have been tied (or otherwise attached) to the tubular braid fibers. These fibers (144) are tied at various intervals to increase the propensity of the device to occlude blood. The outlying fibers (144) are typically Dacron but may be any of the natural and manmade fibers listed above.

Figure 4:
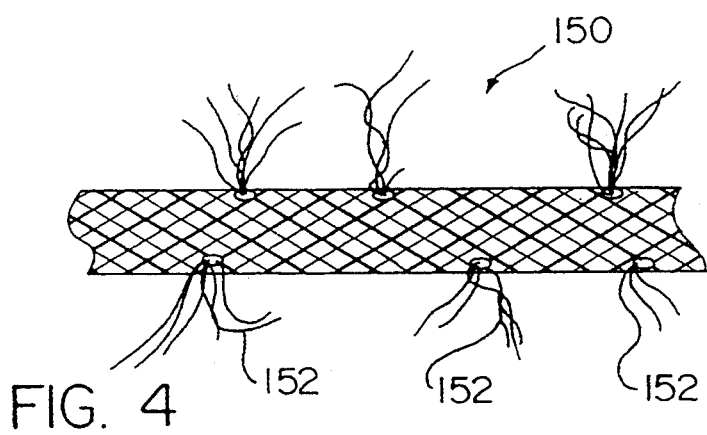

FIG. 4 shows another variation (150) of the inventive device in which tassels (152) are tied to the tubular braid to increase the breadth of the device and increase its overall clotting ability. These tassels are typically Dacron but, again, may be any of the fibrous materials described above. The tassels (152) may be short or long and may be singular or multiple depending upon the use intended.

Figure 5:
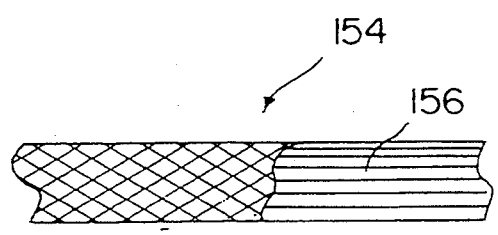

FIG. 5 shows a cutaway sideview of the inventive device in which the braided tubular vasoocclusion device discussed above contains a core of radiolucent fibers. Although the fibers making up the braided tube may be radiolucent or radiopaque, the radiopaque fibers are preferred. The interior core of the braided tubular occlusion device (154) contains a bundle of radiolucent fibers (156) extending from one end of the braided tube to the other. The fiber bundle may be made up of fibers selected from those thermoplastics and natural materials noted above. The ends of the bundle may be sealed by heating those ends where the materials so allow. The bundle may be pre-filled or infused with drugs suitable for later hastening of coagulation after the device is introduced into the selected vascular site. The vasoocclusive device of FIG. 5 may also have outlying fibers attached to the braided tubular element as has been discussed generally above.

The braided occlusion devices may be made in a variety of ways, as should be apparent from the discussion above. The devices may be strung on a guidewire or other similar device for installation, necessitating that the braided tubular device have open ends for passage of the guidewires. The ends may be closed if so desired.

The ultimate shape of the device is a matter of choice. We contemplate that it may be straight, as introduced into the body lumen, or may be "C" shaped, circular, figure "8" random or any other shape desirable to the physician user in view of the physical situation to be resolved.

Modifications of the above-described variations for carrying out the invention which are obvious to those of ordinary skill in the fields of medical device design generally, and vasoocclusion devices specifically, are intended to be within the scope of the following claims.

We claim as our invention:

1. A vasoocclusive device comprising a braided tubular member of braided fibers at least a portion of said braided fibers being radiopaque and at least a portion of said braided fibers being radiolucent and said tubular member having an interior cavity and a proximal and a distal end and is of a size suitable for occluding a chosen site within the human vasculature.

2. The device of claim 1 where the tubular member of braided fibers has a diameter of 0.015 to 0.018 inches.

3. The device of claim 2 where the radiolucent fibers are selected from polyesters, polyglycolic acid, polylactic acid, fluoropolymers, polyamides, and silk.

4. The device of claim 3 where the radiolucent fibers comprise a polyester.

5. The device of claim 1 where the radiopaque fibers comprise metals or polymers.

6. The device of claim 5 where the braided radiopaque fibers are selected from platinum, tungsten, gold, silver, tantalum, and alloys thereof, shape memory alloys, and stainless steels.

7. The device of claim 6 where the braided radiopaque fibers comprise a platinum-tungsten alloy.

8. The device of claim 6 where the braided radiopaque fibers comprise a shape memory alloy.

9. The device of claim 8 where at least a portion of the braided radiopaque fibers comprise Nitinol.

10. The device of claim 1 additionally comprising fibers tied to the braided fibers in the braided tubular member.

11. The device of claim 10 where the fibers tied to the braided tubular member are tied at multiple locations.

12. The device of claim 10 where the fibers tied to the braided fibers are tied so as to form tassels.

13. The device of claim 1 where the braided tubular member contains radiolucent fibers within the interior cavity.

14. The device of claim 13 where the radiolucent fibers in the interior cavity extend from the tubular member's distal end to the tubular member's proximal end.

15. The device of claim 13 where the radiolucent fibers in the interior cavity are selected from polyesters, polyglycolic acid, polylactic acid, fluoropolymers, polyamides, and silk.

16. The device of claim 15 where the radiolucent fibers in the interior cavity comprise a polyester.

* * * * *

UNITED STATES PATENT AND TRADEMARK OFFICE
CERTIFICATE OF CORRECTION

PATENT NO. : 5,423,849

DATED : June 13, 1995

INVENTOR(S) : ENGELSON et al.

It is certified that error appears in the above-indentified patent and that said Letters Patent is hereby corrected as shown below:

Column 3, line 14: change "Nitinol" to --nitinol--.

*Claim 3, column 4, line 32*: insert --braided-- prior to "radiolucent".

*Claim 9, column 4, line 48*: substitute --nitinol-- for "Nitinol".

*Claim 11, column 4, line 52*: insert --fibers-- after "braided", delete "tubular member".

Signed and Sealed this

Thirtieth Day of September, 1997

Attest:

BRUCE LEHMAN

Attesting Officer

Commissioner of Patents and Trademarks